United States Patent
Imran

(10) Patent No.: US 7,430,450 B2
(45) Date of Patent: Sep. 30, 2008

(54) DEVICE AND METHOD FOR TREATING OBESITY

(75) Inventor: Mir A. Imran, Menlo Park, CA (US)

(73) Assignee: Intrapace, Inc., Mountain View, CA (US)

( * ) Notice: Subject to any disclaimer, the term of this patent is extended or adjusted under 35 U.S.C. 154(b) by 226 days.

(21) Appl. No.: 11/281,041

(22) Filed: Nov. 16, 2005

(65) Prior Publication Data

US 2006/0079944 A1  Apr. 13, 2006

Related U.S. Application Data

(62) Division of application No. 10/691,735, filed on Oct. 22, 2003, now Pat. No. 7,054,690.

(51) Int. Cl.
*A61N 1/00*  (2006.01)

(52) U.S. Cl. .................................................. 607/133

(58) Field of Classification Search ............... 607/133, 607/149, 40, 116
See application file for complete search history.

(56) References Cited

U.S. PATENT DOCUMENTS

| 6,454,785 | B2 | 10/1984 | Morgan et al. |
| 6,285,897 | B1 | 1/1985 | Martin et al. |
| 7,054,692 | B1 | 9/1988 | Werner et al. |
| 4,878,905 | A | 11/1989 | Blass |
| 5,423,872 | A | 6/1995 | Cigaina |
| 5,716,392 | A | 2/1998 | Bourgeois et al. |
| 5,876,445 | A | 3/1999 | Andersen et al. |
| 6,009,877 | A | 1/2000 | Edwards |
| 6,205,359 | B1 | 3/2001 | Boveja |
| 6,243,607 | B1 * | 6/2001 | Mintchev et al. .............. 607/40 |
| 6,305,436 | B1 | 10/2001 | Andersen et al. |
| 6,327,503 | B1 | 12/2001 | Familoni |
| 6,355,070 | B1 | 3/2002 | Andersen et al. |
| 6,366,814 | B1 | 4/2002 | Boveja et al. |
| 6,427,089 | B1 | 7/2002 | Knowlton |
| 6,535,764 | B2 * | 3/2003 | Imran et al. .................... 607/40 |
| 6,571,127 | B1 | 5/2003 | Ben-Haim et al. |
| 6,591,137 | B1 | 7/2003 | Fischell et al. |
| 6,606,518 | B1 | 8/2003 | Cigaina |
| 6,675,809 | B2 * | 1/2004 | Stack et al. .................. 128/898 |
| 6,684,104 | B2 | 1/2004 | Gordon et al. |
| 6,754,536 | B2 | 6/2004 | Swoyer et al. |
| 6,826,428 | B1 | 11/2004 | Chen et al. |
| 6,879,859 | B1 | 4/2005 | Boveja |
| 6,895,278 | B1 | 5/2005 | Gordon |
| 6,895,279 | B2 | 5/2005 | Loeb et al. |
| 7,020,526 | B1 | 3/2006 | Zhao |
| 2002/0072780 | A1 | 6/2002 | Foley |

(Continued)

FOREIGN PATENT DOCUMENTS

WO  WO 9843700  10/1998

(Continued)

*Primary Examiner*—Carl Layno
*Assistant Examiner*—Jon-Eric C Morales
(74) *Attorney, Agent, or Firm*—Townsend & Townsend & Crew LLP; Mark D. Barrish

(57) ABSTRACT

A device and method are provided for treating obesity by implanting an electrode in the duodenum and stimulating the duodenum with a stimulator, causing the pylorus to contract.

6 Claims, 11 Drawing Sheets

U.S. PATENT DOCUMENTS

| | | | |
|---|---|---|---|
| 2002/0161414 A1 | 10/2002 | Flesler et al. | |
| 2002/0165589 A1* | 11/2002 | Imran et al. | 607/40 |
| 2002/0183237 A1 | 12/2002 | Puskas | |
| 2002/0183768 A1* | 12/2002 | Deem et al. | 606/151 |
| 2002/0198470 A1* | 12/2002 | Imran et al. | 600/587 |
| 2002/0198570 A1 | 12/2002 | Puskas | |
| 2003/0055463 A1 | 3/2003 | Gordon et al. | |
| 2003/0120328 A1 | 6/2003 | Jenkins et al. | |
| 2003/0125788 A1 | 7/2003 | Long | |
| 2003/0144708 A1 | 7/2003 | Starkebaum | |
| 2003/0195600 A1 | 10/2003 | Tronnes et al. | |
| 2003/0212439 A1 | 11/2003 | Schuler et al. | |
| 2004/0015201 A1 | 1/2004 | Greenstein | |
| 2004/0044376 A1 | 3/2004 | Flesler et al. | |
| 2004/0059393 A1 | 3/2004 | Policker et al. | |
| 2004/0088022 A1 | 5/2004 | Chen | |
| 2004/0093039 A1 | 5/2004 | Schumert | |
| 2004/0107004 A1* | 6/2004 | Levine et al. | 623/23.64 |
| 2004/0133089 A1 | 7/2004 | Kilcoyne et al. | |
| 2004/0147816 A1 | 7/2004 | Policker et al. | |
| 2004/0162595 A1 | 8/2004 | King | |
| 2004/0172084 A1 | 9/2004 | Knudson et al. | |
| 2004/0172085 A1 | 9/2004 | Knudson et al. | |
| 2004/0172086 A1 | 9/2004 | Knudson et al. | |
| 2004/0172095 A1 | 9/2004 | Jenkins et al. | |
| 2004/0176812 A1 | 9/2004 | Knudson et al. | |
| 2004/0236381 A1 | 11/2004 | Dinsmoor et al. | |
| 2004/0236382 A1 | 11/2004 | Dinsmoor et al. | |
| 2005/0021101 A1 | 1/2005 | Chen et al. | |
| 2005/0049655 A1 | 3/2005 | Boveja et al. | |
| 2005/0055039 A1 | 3/2005 | Burnett et al. | |
| 2005/0065575 A1 | 3/2005 | Dobak | |
| 2005/0113880 A1 | 5/2005 | Gordon | |
| 2005/0222637 A1 | 10/2005 | Chen | |
| 2005/0222638 A1 | 10/2005 | Foley et al. | |
| 2006/0025654 A1 | 2/2006 | Suzuki | |
| 2006/0074335 A1 | 4/2006 | Ben-Oren | |
| 2006/0116736 A1 | 6/2006 | Dilorenzo | |

FOREIGN PATENT DOCUMENTS

| | | |
|---|---|---|
| WO | WO 0030534 | 6/2000 |
| WO | WO 0176690 | 10/2000 |
| WO | WO 0226101 | 4/2002 |

* cited by examiner

DEVICE AND METHOD FOR TREATING OBESITY

This application is a Divisional patent application of U.S. patent application Ser. No. 10/691,735, filed Oct. 22, 2003 now U.S. Pat No. 7,054,690.

FIELD OF THE INVENTION

The invention relates to a stimulation device and method for stimulating a portion of the gastrointestinal tract and in one particular embodiment to a device and method for stimulating the duodenum to control the pylorus and/or to treat obesity.

BACKGROUND OF THE INVENTION

In general when food is ingested into the stomach, initially, the elastic upper portion or fundus accommodates the food and the fundus expands. As food enters and the fundus expands there is a pressure gradient created in the stomach between the fundus and the antrum (fundus pylori). A number of things occur at this time. Fluids tend to be pushed through the pylorus, which acts as a leak valve. Peristaltic contractions move down the stomach from the fundus into the antrum to mix and break down food and propel small articles through the pylorus into the duodenum. In healthy human stomachs, peristalsis is believed to be controlled at least in part by a region of the stomach identified near the interface of the fundus and the corpus along the greater curvature. In this region, there are cells believed to govern the organs' periodic contractile behavior that generate and propagate rhythmic electrical signals that correspond to the contractile behavior of the stomach. These characteristic contractions are believed to create, a pressure gradient between the fundus pylori (or antrum) and duodenum that relates to the rate of gastric emptying. When the contractions begin, the pylorus is generally closed, although fluid and small particles leak through the valve. As contractions or electrical activity corresponding to the contractions reach pylorus, the pylorus begins to open or relax. Thus, as the stomach churns and breaks down food in a healthy stomach, the pylorus begins to open. As this is occurring, there may be electrical activity in the duodenum as well. Retrograde electrical activity from the duodenum, i.e. contractions or electrical activity in the direction of the pylorus tends to cause the pylorus to close, thus preventing bile and pancreatic juices from backing up into the stomach. Accordingly, the opening and closing of the pylorus is influenced by electrical stimulation input from both of its ends.

In a number of disease states or conditions, the contractions of the stomach and/or the opening and closing of the pylorus is irregular. Gastroparesis may result from insufficient contractions to churn food, move food through the pylorus, and/or open the pylorus, among other things, resulting in gastro-retention of food. In another motility disorder known as dumping syndrome, the stomach empties at an abnormally high rate into the small Intestine causing various gastrointestinal disorders. It has also been observed that in obese patients, gastric emptying tends to be at a higher than normal rate. It is believed that obesity may be treated by altering gastric motility to cause the stomach to slow gastric emptying.

Accordingly, it would be desirable to provide a device and method for controlling gastric emptying. Further, it would be desirable to provide a device and method that controls the contracting and relaxation of the pylorus according to a desired increase or decrease in gastric emptying.

Some devices have been proposed to constrict the stomach to reduce stomach volume. These devices are typically implanted in a relatively invasive procedure and operate to constrict the stomach but do not enable periodic control of the stomach emptying. Some devices have been proposed to interfere with the peristaltic motion of the gastrointestinal tract and especially the stomach, to slow the movement of food from the stomach. These devices control the contractions of the stomach but are not directed to opening and closing the pylorus outside of the context of controlling peristalsis of the stomach. Furthermore, most of these devices require open or laparoscopic surgery in which a stimulator unit is implanted subcutaneously adjacent the abdomen wall with leads extending to the stomach where electrodes are attached. Artificial sphincters, for opening and closing sphincters including the pylorus have been proposed. These devices typically involve placing a constricting member around the sphincters in a relatively invasive procedure.

Accordingly it would be desirable to provide a relatively easily implanted device and method for controlling the opening and/or closing of the pylorus. It would further be desirable to provide a method and device or treating obesity.

SUMMARY OF THE INVENTION

The invention provides a fixation device for holding stimulating electrodes in electrical contact with the wall of a portion of the gastrointestinal tract. In one embodiment, the fixation device includes an expandable member that fixes the electrodes in electrical contact with the gastrointestinal tract wall. According to one embodiment, the fixation device comprises a relatively tubular shaped structure that holds stimulating electrodes adjacent the wail of the duodenum while permitting the passage of materials through the device. According to another embodiment of the invention, the fixation device comprises a self-expanding tubular member.

The present invention further provides an implantable device and method for controlling the opening and/or closing of the pylorus. In particular, one embodiment comprises a device and method for stimulating the duodenum to control the closing/and or opening of the pylorus. According to this embodiment, electrodes are coupled to the wall of the duodenum. In one embodiment, the electrodes are coupled to the duodenum above the duct through which bile and pancreatic secretions empty into the small intestine. Electrical stimulation pulses are delivered by an electronic circuit through the electrodes. The stimulation pulses that travel in a deep retrograde direction end to cause the pylorus to contract and close. The stimulation may be delivered after sensing a meal or that food has been ingested. For example, detecting a change in temperature due to food particles not at body temperature. Or, the stimulation may be user activated whereby the user turns on the device asker ingesting a meal. The stimulation in one embodiment is sew to continue for a predetermined period of time. Thus, where a patient's typical rate of gastric emptying is greater that desired, such emptying may be slowed using the stimulator.

The present invention also provides a method for treating obesity by controlling the pylorus to retain food in the stomach for a desired period of time, among other things to provide a feeling of satiety and/or to reduce hunger. According to one embodiment, the pylorus's contraction is controlled by electrical stimulation of the duodenum. The retrograde propagation of the stimulation acts to close or cause contraction of the pylorus.

DETAILED DESCRIPTION OF THE INVENTION

Figure 1:
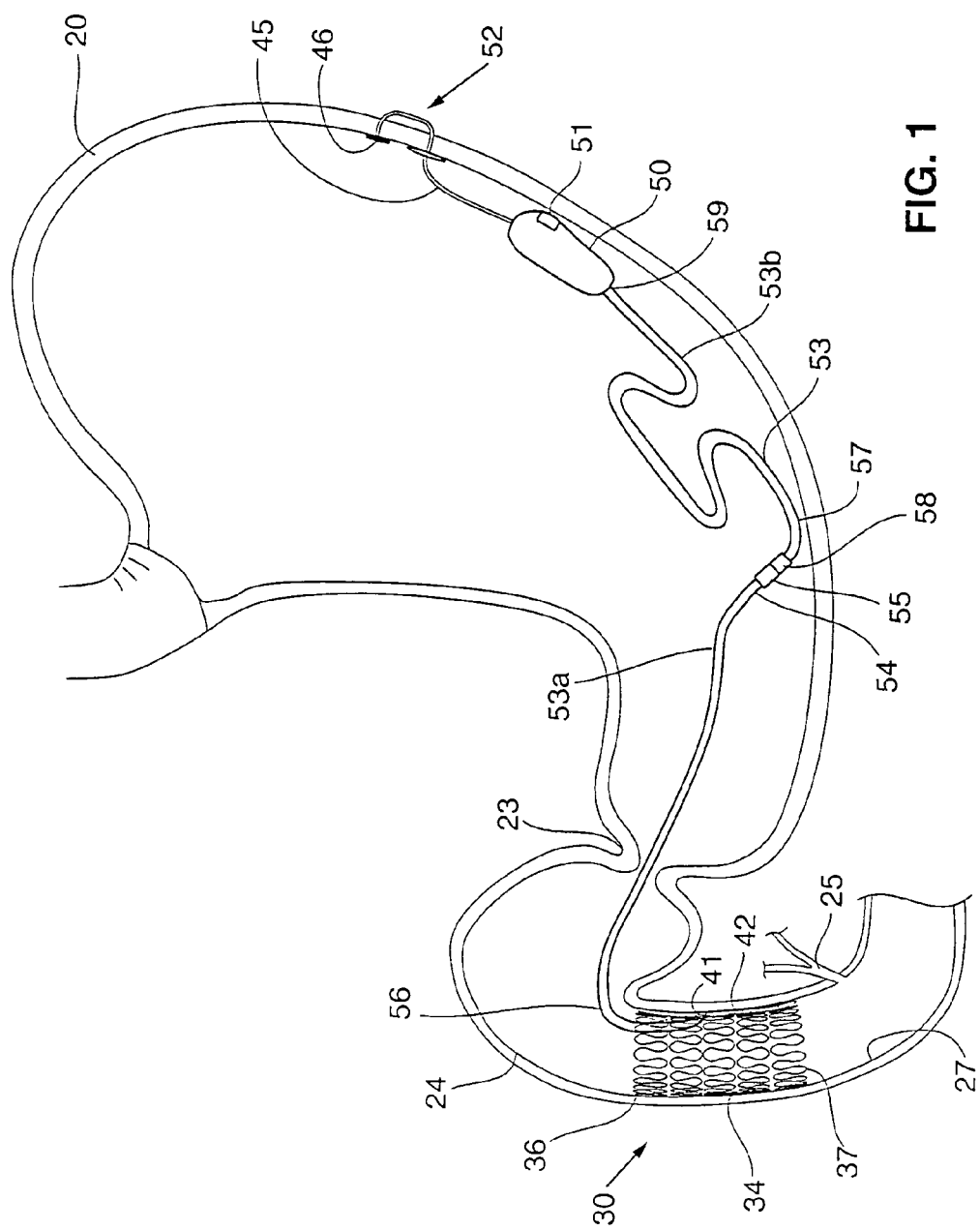
FIG. 1 is a side cutaway view of a stomach and duodenum with an implanted stimulator according to an embodiment of the invention.

Referring to FIGS. 1 and 1A-1F a stimulator 30 in accordance with the invention is illustrated implanted in the gastrointestinal tract of a patient. The stimulator 30 comprises a fixation device 34 to be implanted in the duodenum 24 and an electronics housing 50 to be located in the stomach 20 and coupled by wire tube 53 enclosing leads 51, 52, to the fixation device 34. The fixation device 34 includes electrodes 41, 42 in electrical contact with the duodenum 24 and the electronics housing 50 includes electronic circuitry 125 and a battery 144 that supply electrical stimulation pulses to the duodenum 24 through the electrodes 41, 42.

In FIG. 1, the fixation device 34 is illustrated in place in the duodenum 24 located adjacent the pylorus 23 of a patient and above the duct 25 (where the ducts for bile and pancreatic secretions merge). The electrodes 41, 42 of the fixation device 34 are contained in an electrode housing 43 (FIG. 1A) and exposed at the outer circumference of the fixation device 34 so that the electrodes 41, 42 may be positioned in electrical contact with the wall 27 of the duodenum 24. The fixation device 34 operates to engage the inner circumference of the wall 27 of the duodenum 24 to hold and maintain the electrodes 41, 42 in electrical contact with the duodenum 24. The fixation device 34 comprises a plurality of rings 36 including undulating members 37 having peaks and valleys that permit compression and expansion of the rings 36. The rings 36 are preferably formed of Nitinol to provide spring-like properties with sufficient radial strength so that they may be compressed and constrained by a catheter containing the fixation device 34, and released from the catheter to expand into an expanded engaging position within a lumen of the gastrointestinal tract. The rings 36 define a common axis 39 extending through the rings 36. The rings 36 are attached to each other by way of the electrode housing 43, which is molded onto the rings 36 along the axis 39 of the rings 36. Each ring 36 is formed by a closed wire loop of undulating members 37 and includes a straight portion 38 over which the electrode housing 43 is molded. The electrode housing 43 may be formed of a biocompatible elastic such as polyurethane or polycarbonate. The fixation device 34 further defines a lumen 45 extending along the axis 39 through which materials from the stomach 20 may pass.

Figure 1A:
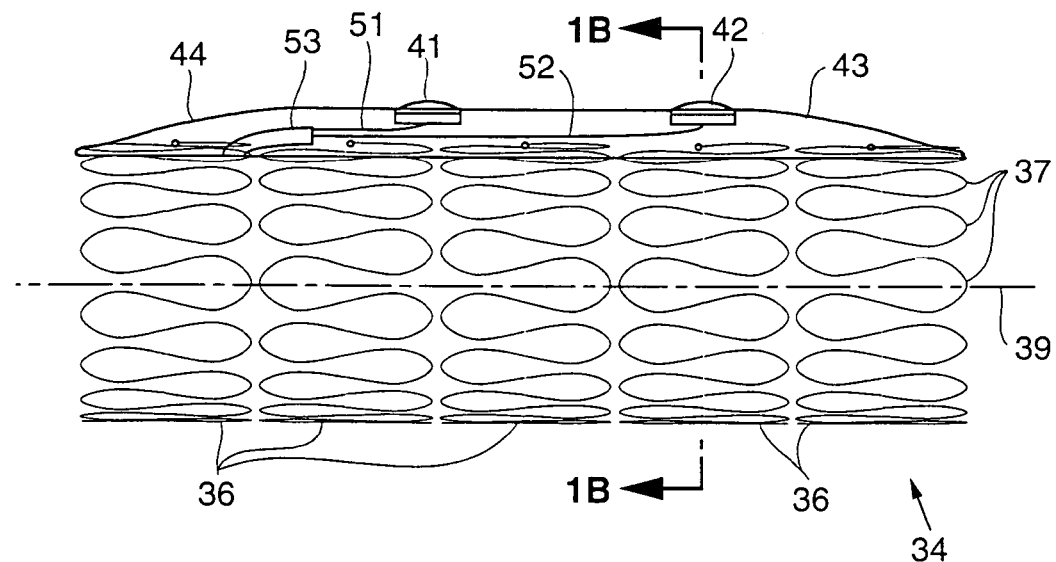
FIG. 1A is a side view of the fixation device of the stimulator of FIG. 1 in a compressed configuration.
Figure 1B:
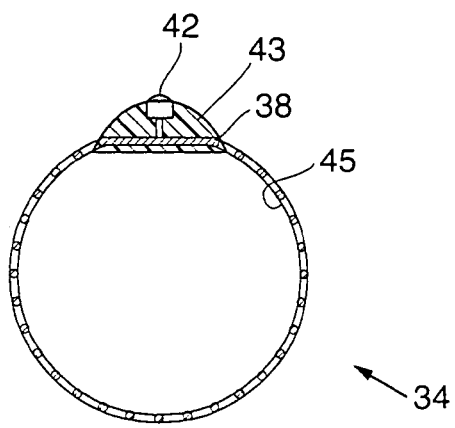
FIG. 1B is a cross sectional view or FIG. 1A along the lines 1B-1B.
Figure 1C:
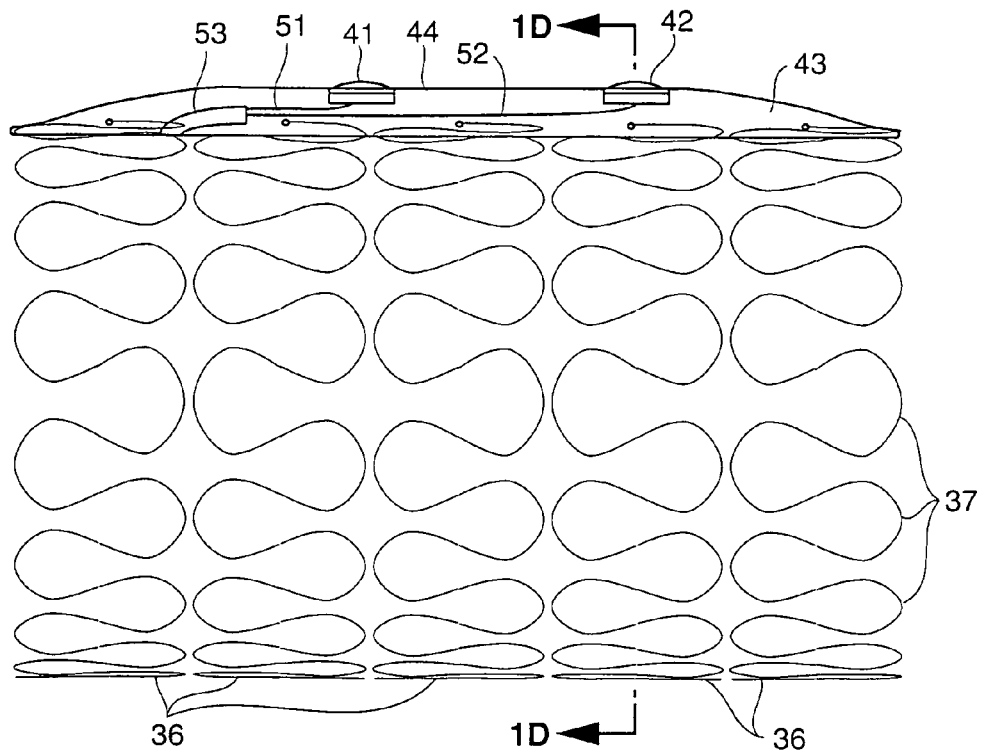
FIG. 1C is a side view of the fixation device of the stimulator of FIG. 1 in an expanded configuration
Figure 1D:
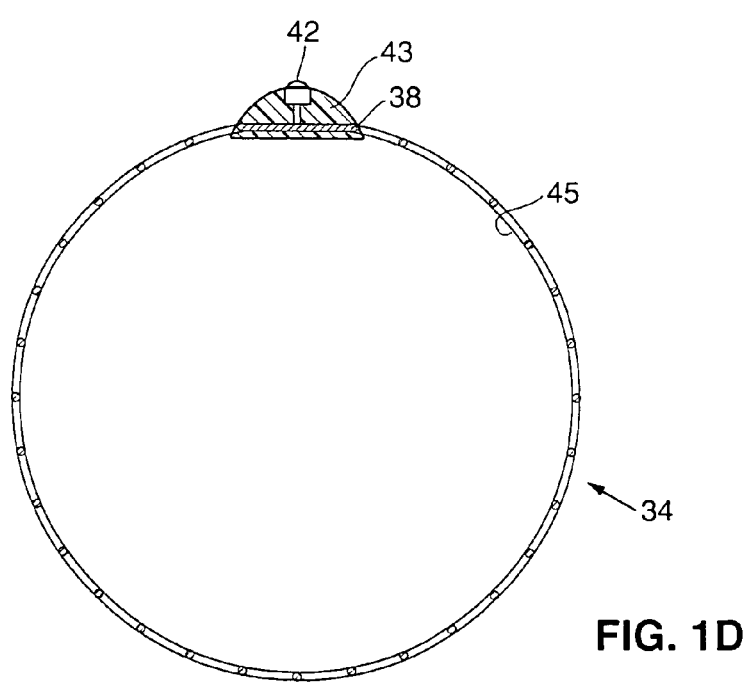
FIG. 1D is a cross-sectional view of FIG. 1C along the lines 1D-1D.
Figure 1E:
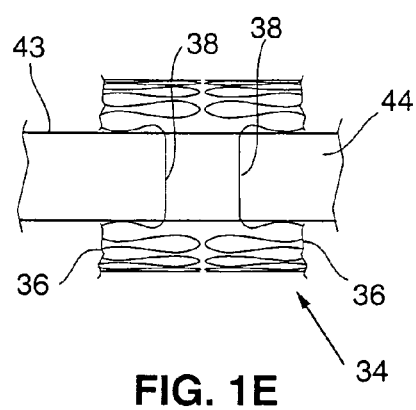
FIG. 1E is a top view of a portion of the stimulator illustrated in FIG. 1A.
Figure 1F:
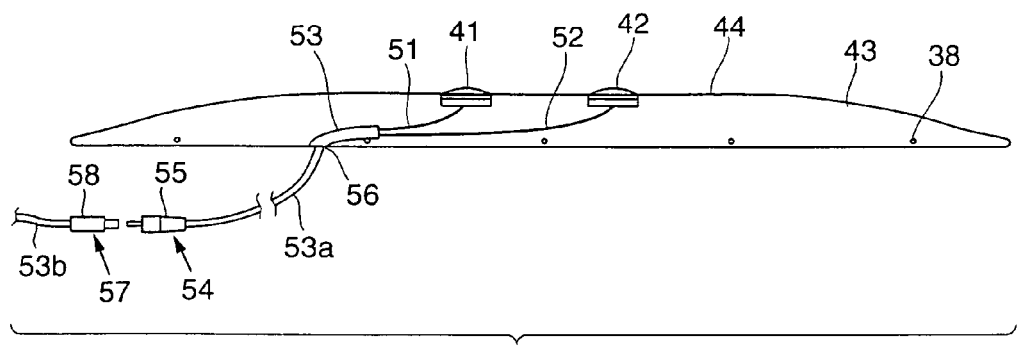
FIG. 1F is a schematic side view of the electrode housing of the stimulator of FIGS. 1, and 1A-1E.

The fixation device 34 may delivered in a compressed configuration to the duodenum 24 through a catheter or the like, containing the fixation device 34 in its compressed state. The fixation device is then expanded into a configuration in which it engages the wall 27 of the duodenum 24. As illustrated in FIGS. 1A and 13, in a compressed position, the diameter of the fixation device 34 is relatively small so that it can reside with within a catheter of sufficiently small diameter to be placed through upper gastrointestinal tract (i.e., into the mouth of a patient, through the esophagus and stomach, and through the pylorus into the duodenum). The catheter may include a retractable sheath containing the fixation device 34. The sheath is retractable upon locating the catheter in a desirable position for deployment of the fixation device 34 in the duodenum 24. This may be guided by and endoscope or fluoroscopy. The fixation device 34 should be position in an orad location from the duct 25 where the bile and pancreatic secretions empty into the duodenum 24 so that the fixation device 34 does not block the duct 25. When retracted, the sheath permits the self-expanding rings 36 of the fixation device 34 to expand to the expanded position illustrated in FIGS. 1C and 1D. Thus, when released from the catheter, the fixation device 34 expands to engage the inner circumference of the wall 27 of the duodenum 24. In its expanded position, the circumference of the fixation device 34 increases while the electrode housing 43 and the straight portion 33 of each ring 36 encased by the electrode housing 43 maintain their original size and shape. The radial strength of the rings 36 serves to hold the fixation device 34 in place. The electrodes 41, 42 are located on the outer surface 44 of the electrode housing 43 and the rings 306 hold them in place against the wall 27 of the duodenum 24 to provide electrical contact therewith. Alternatively, the rings 36 may be expandable by a balloon catheter or the like.

Figure 5:
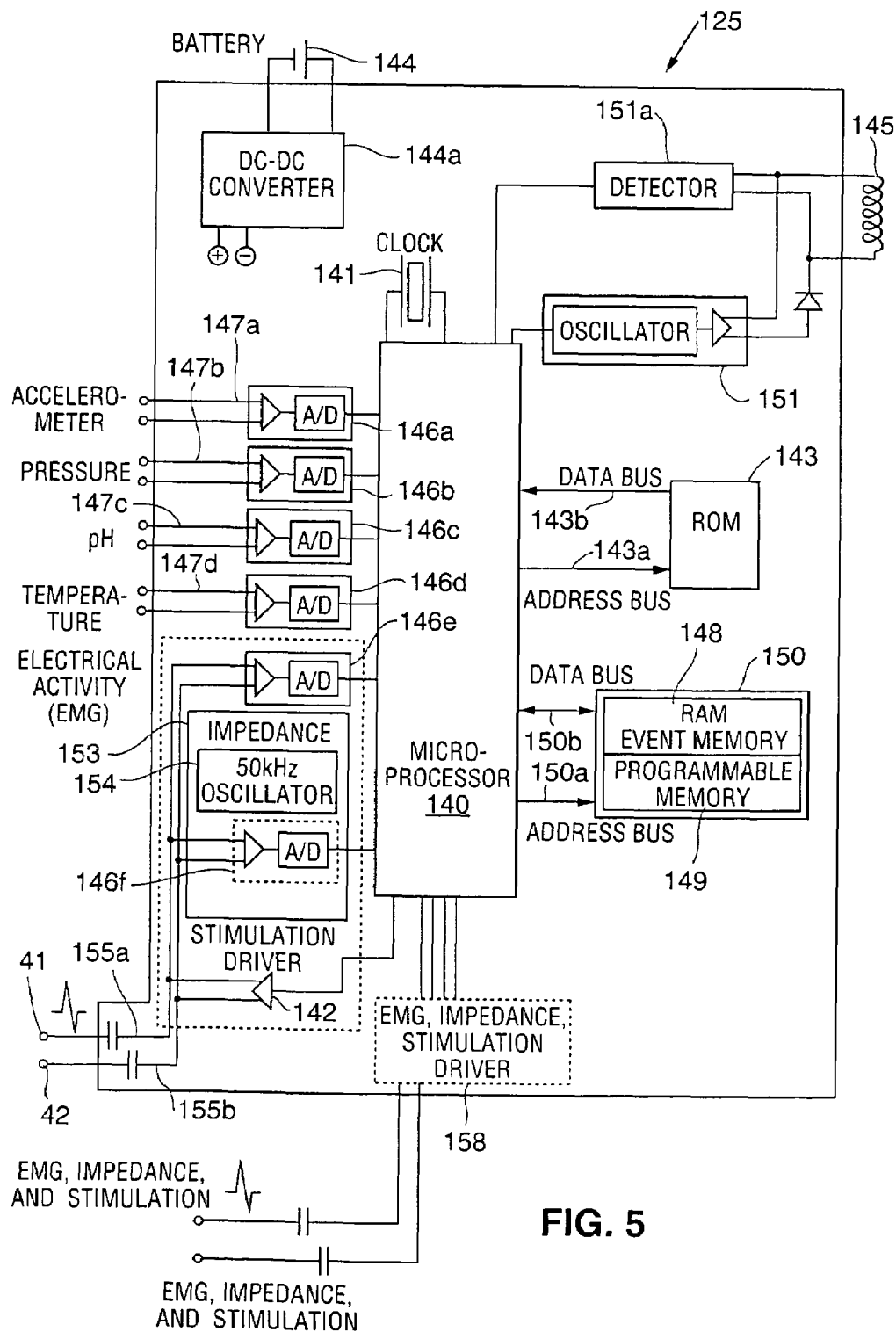
FIG. 5 is a schematic of an electronic circuit of a stimulator according to an embodiment of the invention.

A pair of leads 51, 52 encased in a tube 53 extend out of the fixation device 34 and are coupled to the electronics housing 50. When the fixation device 34 is deployed, the tube 53 and electronics housing 50 extend in an orad direction, through the pylorus 23 and into the stomach 20. The electronics housing 50 is attached to the stomach 20 wall leaving sufficient slack in the tube 53 to allow for stomach contractions and movement. In this embodiment, the electronics housing 50 contains a battery 144 and electronic circuitry 125 (FIG. 5) for providing electrical stimulation to the duodenum 24 through the leads 51, 52 extending thorough tubing 53 and coupled to the electrodes 41, 42. FIG. 5 illustrates exemplary electronics 125 and battery 144 that may be used with the stimulator 30 or stimulators of other embodiments of the invention, such as, for example, those described herein. The electronics housing 50 also includes a sensor 51 (or plurality of sensors) that may be provided with the capability of sensing one or more or various parameters or the gastrointestinal tract such as, e.g., pressure, temperature, pH, and relative movement (e.g., using an accelerometer).

The electronics housing 50 may be delivered into the stomach and coupled to the fixation device 34 in a number of manners. With the fixation device 34 in position in the duodenum 24, the electronics housing 50 may be delivered to the stomach and attached to the fixation device through the wire tubing 53 extending between the stomach 20 and the duodenum 24 by connecting the wire tubing of a first portion 53a attached to the fixation device 34, to a second portion 53b of the wire tubing 53 coupled to the electronics housing 50. The first portion 53a has a free end 54 with a connector 55 and an attached end 56' attached to the electrodes 41, 42 through the electrode housing 43 on the fixation device 34. The second portion 53b includes an attached end 59 coupled to the electronics housing 50 and a free end 57 having a connector 58 that will mate with the connector 55 on the free end 54 of the first portion 53a to provide a connected electrical leads between the electrode housing 43 and the electronics housing 50. The electronics housing 50 is secured to the stomach wall with an attachment mechanism 52 and so that the tube 53 has sufficient slack to permit stomach churning, while not damaging or pulling the housing 50, fixation device 34 or tube 53. The attachment mechanism 52 prevents the housing 50 from moving through the pylorus 23. The attachment mechanism 52 comprises an elongate flexible member 45 attached to the housing 50 and extending through the stomach wall and having a T-shaped end 46 that attaches the elongate member 45 to the stomach wall.

The electronics housing 50 may be delivered into the stomach and attached to the stomach wall using a needle into which the T-shaped end 46' is loaded. The needle pierces the stomach wall and releases the T-shaped end 46. The housing 50 is then attached to the fixation device 34 by using grasping tools extending through tool channels of an endoscope, to attach connectors 55 and 58. The electronics housing 50 may also be detached from the fixation device 34 through connectors 55, 58 so that the battery 144 and/or electronics 125 may be replaced. While the electronics housing 50 and fixation device 34 are illustrated as being connected after the fixation device 34 and electrode housing 43 have been deployed, the electronics housing 50 may also be deployed through the catheter in a connected position with the fixation device before or after the fixation device 34 has been positioned and deployed. A catheter accommodating a needle to attach the attachment device 52 and a deployment mechanism for the fixation device 34 would need to be accommodated in a catheter designed for the multiple tasks involved.

The electronics housing 50 has a round smooth shape that will minimize any trauma to the stomach. The electronics housing 50 is also of a sufficient size that it will not be passed through pylorus 23 into the duodenum 24. It is further constructed of a material that resists corrosion in the highly acidic stomach environment. Such corrosion resistant materials may include, for example, an acid corrosion resistant material such as a suitable inert polymer, for example, materials from the Polyolefin family like HDPE (high density polyethylene), LLDPE (linear low density polyethylene), and UHMWPE (ultra high molecular weight polyethylene); fluoropolymer materials like PTFE™ (poly tetrafluoroethylene), FEP™ (fluorinated ethylene propylene) and others; polymethylpentene, and polysulphons; some elastomers such as thermoplastic polyurethanes and C-Flex type block copolymers that are stable in acidic environments. Additionally the electronics housing 50 may be constructed of an acid corrosion resistant metal such) as Platinum, Gold, Tantalum, Titanium, or suitable alloys thereof.

Referring to FIG. 5, the electronics 125 and battery 144 are illustrated that may be used with the various embodiments of the stimulator described herein. The electronic circuitry may be on a chip or otherwise have a standard configuration that may be used in a number of different embodiments of the stimulator device. In general, the electronic circuitry includes a controller that delivers electrical stimulation pulses through the electrodes to the wall of the duodenum, the stimulation tends to cause the pylorus 23 to close. The stimulation may be actuated by a user upon ingesting food and the stimulation may continue for a predetermined period of time thereafter. In one embodiment the stimulation parameters are preprogrammed into the controller. The stimulation device may also be provided with the capability of sensing various parameters of the gastrointestinal tract such as, e.g., pressure, temperature and relative movement (e.g., using an accelerometer). The parameters may be used to determine various conditions, for example, patient is awake, sleeping and the type, period, or other parameters of stimulation may be modified according to a program or by a user or health care provider. The electronic circuitry 125 of the stimulator is located in the stimulator housings of the various implants described herein such as, for example, a subcutaneously implanted stimulator unit; a stimulator unit included with the fixation device; a removable attachable housing that may be attached to the fixation device; or in a another housing located within the gastrointestinal tract (e.g., the stomach) and attached by way of leads to the fixation device. Likewise, the battery 144 that powers the electronic circuitry 125 may be located in a number of different housings in various embodiments and configurations of the stimulator. In these different locations, the battery 144 may be removable and replaceable with the electronic circuitry 125 or own its own in a modular device. If the stimulator is included with the fixation device, the battery may also be removably and replaceably attachable to the electronics or electrode housing on the fixation device. The battery 144 may be located with the electronic circuitry 125 attached by way of leads to the stimulator.

The stimulation of the duodenum occurs for a predetermined period of time after which the stimulation is discontinued to allow emptying of the stomach. The circuitry 125 of one embodiment as illustrated in FIG. 5 comprises: a microprocessor or controller 140 for controlling the operations of the electronic circuitry 125, and an internal clock 141. The circuitry 125 may also include a battery device 144 such as a pair of lithium iodine batteries for powering the various components of the circuitry 125. Alternatively, the battery device 144 may be housed in a separate unit that may be coupled to the circuitry 125. As such, the controller 140 and battery device 144 are coupled to each of the major components of the circuit as would be apparent to one of ordinary skill in the art. The controller 140 is coupled to stimulation driver 142, which is coupled to stimulating electrodes 41, 42 (or an of the other electrodes described herein) that are used to provide electrical stimulation in accordance with programmed parameters.

The controller 140 is coupled to ROM 143, which contains the program instructions for the controller 140 and any other permanently stored information that allows the microprocessor/controller 140 to operate. The controller 140 addresses memory in ROM 143 through address bus 143a and the ROM 143 provides the stored program instruction to the controller 140 via data bus 143b. The controller 140 controls the RF coil 145, which communicates with an external control or programming device 160 (FIG. 6), preferably via a modulated RF signal. Processor 140 is coupled to a buffered oscillator 151 that provides an RF signal to be emitted from the RF coil 145. The RF signal is preferably at about 100 kHz to 5 MHz so that the signal is efficiently transmitted through tissue. The controller 140 controls the oscillator 151 and may provide data to be modulated with the RF signal to be delivered through the RF coil 145. Such data mat include, for example, data sensed by a sensor 51 located on the electronics housing 50 (or alternatively the fixation device 34), such as pressure, pH, temperature, movement (accelerometer), or sensed electrical information such as impedance, electrical activity (EMG) etc. One or more sensors 147a (e.g., accelerometer), 147b (e.g., pressure), 147c (e.g., pH), 147d temperature, or electrodes 41, 42 (for sensing EMG, EGG, or impedance as well as providing stimulation), may be coupled to the controller 140 through A/D converters (with amplifiers) 146a, 146b, 145c, 140d, 145e which convert a representative analog electrical signal into a digital signal. Suitable types of these sensors are generally known in the art and may be located within, on, or external to the electronics housing 50, fixation device 34 or electrode housing 43 on the fixation device 44. When the RF coil 145 is receiving an external telemetry signal, the buffered oscillator 151 is disabled. Telemetry signals received on the Rev coil 145 are detected in a detector circuit 151a and to communicated controller 140. The detector circuit 151a is preferably selected based on the modulation used for telemetry signals. The sensed parameters may indicate e.g. the ingestion of food or activity level of a patient. Pacing may be turned on or off based on these parameters.

Controller 140 is coupled to Rail 150 via an address bus 150a for addressing a location in RAM 150 and a bi-directional data bus 150b for delivering information to and from RAM 150. The RAM 150 includes event memory 148 that temporarily stores data recorded by sensors 147a-d or electrodes 41, 42 (or other electrode pairs described herein). RAM 150 also includes a programmable memory 149 which may be programmed, for example, by an external programmer 160. The data stored in the programmable memory may include specifications for the electrical stimulation operating modes or parameters. Such programming may be done in response to sensed information or it may be done automatically by an external controller or as desired by a treating physician, etc. Sensed data acquired from sensors 147a-d and electrodes 41, 42 or other electrode pairs described herein, provided to the controller 140 may be stored in event memory 148 in the RAM 150. The data stored in the event memory 148, may be sent intermittently as data bursts via the RF coil 145, as opposed to continuously in order to save battery power.

The electrode 41, 42 outputs are used to provide electrical stimulation delivered through the stimulation driver 142 to the 41, 42. The stimulation modes and parameters may be pre-programmed or may be set using the external programmer 160 or in response to sensory feedback. The same electrode cutouts may be used to sense impedance through impedance circuit 153 and to sense electrical activity, which is delivered through A/D converter 146e. The electrodes 41, 42 are coupled through coupling capacitors 155a and 155b respectively, to the output of electrical stimulation driver 142 and the inputs of A/D converters 146e, 146f.

The impedance circuit 153 comprises a constant current source oscillator 154 that oscillates at a frequency of 50-100 kHz, and an A/D converter 146f coupled to the controller 140. The oscillator 154 provides a constant current source through electrodes 41, 42 resulting in a voltage across the electrodes 41, 42 that is representative of impedance, in view of the constant current. The voltage is provided through and is converted by A/D converter 146f to a digital signal representative of impedance. A/D converter 146f has a bandwidth that includes the 50 kHz frequency signal while filtering out the electrical stimulation signal that is delivered to the electrodes 41, 42 through electrical stimulation driver 142, and the EMG signal that is sensed by the electrodes 41, 42. Both of the outputs are filtered out by A/D converter 146f. A/D converter 146e has a bandwidth that filters out the 50-100 kHz signal. Further, when a stimulation signal is being delivered, the controller 140 does not receive signals from A/D converters 146e and 146f. Thus the EMG and impedance sensing functions and the stimulation delivery functions are separated through the electronic circuitry 125, though using the same electrodes.

The battery 144 has its output supplied to a DC-to-DC converter 144a to provide a higher voltage, which is utilized for electrical stimulation pulses. The DC-to-DC converter 144a is conventional and provides an output voltage of 15 to 20 volts.

Figure 6:
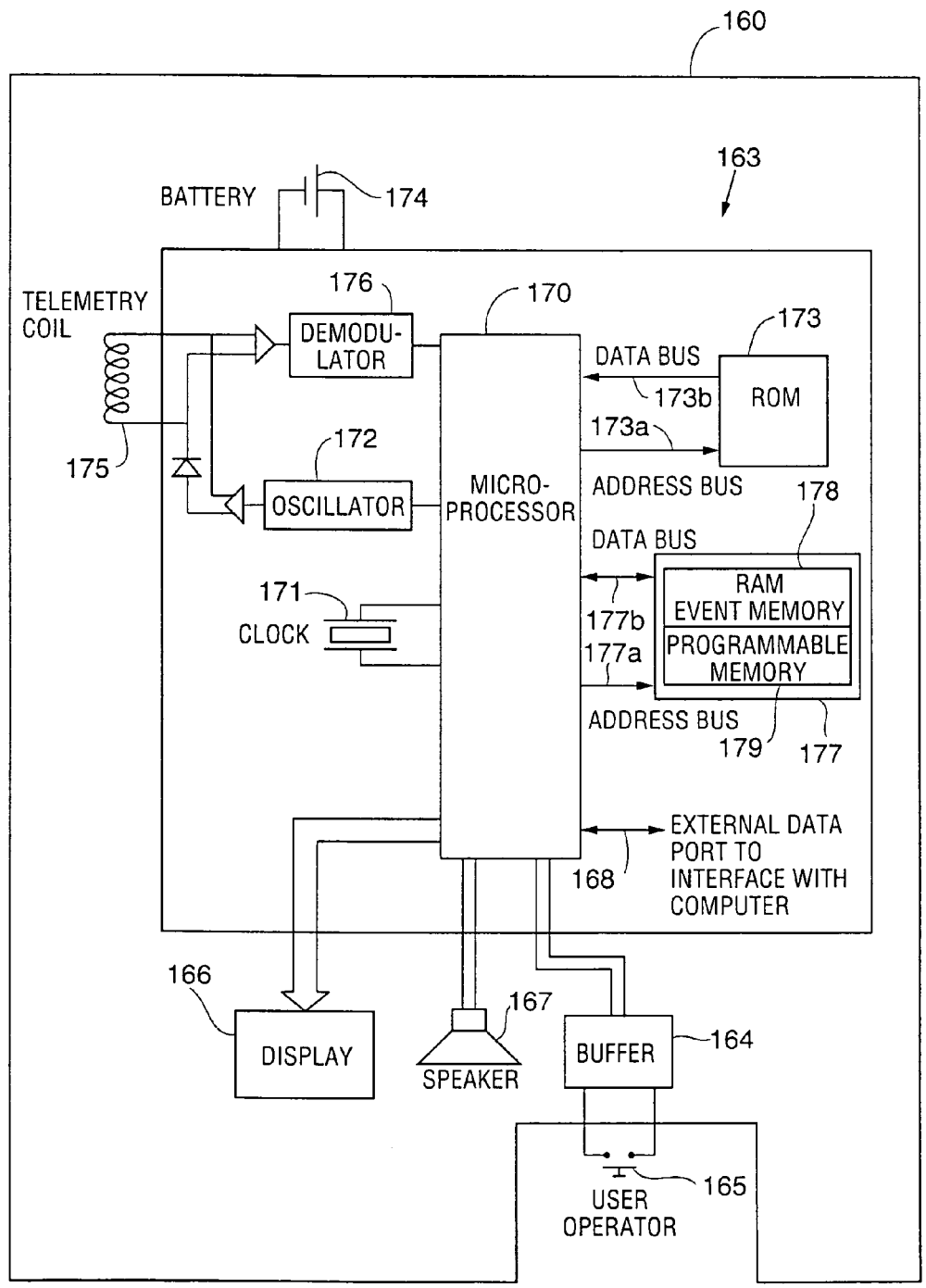
FIG. 6 is a schematic of an external controller circuit according to an embodiment of the invention.

FIG. 6 illustrates the electronic circuitry 163 for external programmer 160. The electronic circuitry 163 comprises: a microprocessor or controller 170 for controlling the operations of the electronic circuitry, an internal clock 171, and a power source 174 such as a battery device for powering the various components of the circuit 163. As such, the controller 170 and battery device 174 are coupled to each of the major components of the circuit as would be apparent to one of ordinary skill in the art. The controller 170 may be coupled to a speaker 167 for that provides audible alerts and a display 166 such as a CRT to display data such as recorded data, sensed parameters, treatment parameters and status of the device (e.g. position or battery charge status). The controller 170 is coupled through a buffer 164 to external input device 165 that is used to provide program parameter input, e.g. from a user, for a user to request data displayed in a desired format through display 166 or speaker 167, or to turn the device on and off. The external programmer 160 is also provided with an external data port 168 co interface with a computer and provide a means for bi-directional communication of data or commands. The computer may provide programming or data to the controller/microprocessor 170. A user may also interface with the computer to provide treatment protocols or changes in protocols, etc. Also, a user may control the turning on and off of the stimulation program.

The controller 170 is coupled to ROM 173, which contains the program-instructions for the controller 170 and any other permanently stored information that allows the microprocessor/controller to operate. The controller 170 addresses memory in ROM 173 through address bus 173a and the ROM 173 provides the scored program instructions to the controller 170 via data bus 173b. The controller 170 controls the RF coil 175, which communicates with stimulator electronic circuitry 125 (FIG. 5) through its RF coil 145. Processor 170 is coupled to an oscillator 172 that provides an RF signal, preferably having a characteristic frequency of 500 kHz or higher, to be emitted from the RF coil 175. The controller 170 controls the oscillator 172 and provides data to be modulated with the RF signal, for example, programming information, stimulation parameters, etc. The RF coil 175 also receives information transmitted via RF signal from RF coil 145 on the stimulator electronic circuitry 125 such as various sensed data, e.g., pressure, pH, impedance, electrical activity (EMG) etc. The received RF signal is passed through demodulator 176 and is transmitted to the controller 170. The data is delivered to the event memory 178 in RAM 177 by way of data bus 177b for temporary storage. The data may be retrieved from RAM 177 by addressing the storage location via the address bus 177a.

Event memory 178 temporarily stores data recorded by sensors 147a-147 and electrodes 41, 42 and delivered via telemetry to the external programmer 160, until the data is downloaded onto a computer using the external data port 168. The RAM 177 also includes a Programmable memory 179 which may be programmed, for example, to specify operating modes such as waveform, frequency, etc. which programming is then telemetrically communicated to the stimulator electronic circuitry 125. The modes and parameters can either be set using an external programmer 160 or set in response to sensory feedback.

In an alternative embodiment, the device includes a housing, electrodes and minimal electronics and an electromagnetic coil. This device is powered by an external electromagnetic coil, which is placed on the patient's abdomen near the implanted device. The electrical stimulation parameters are controlled real-time by an external unit.

Figure 2:
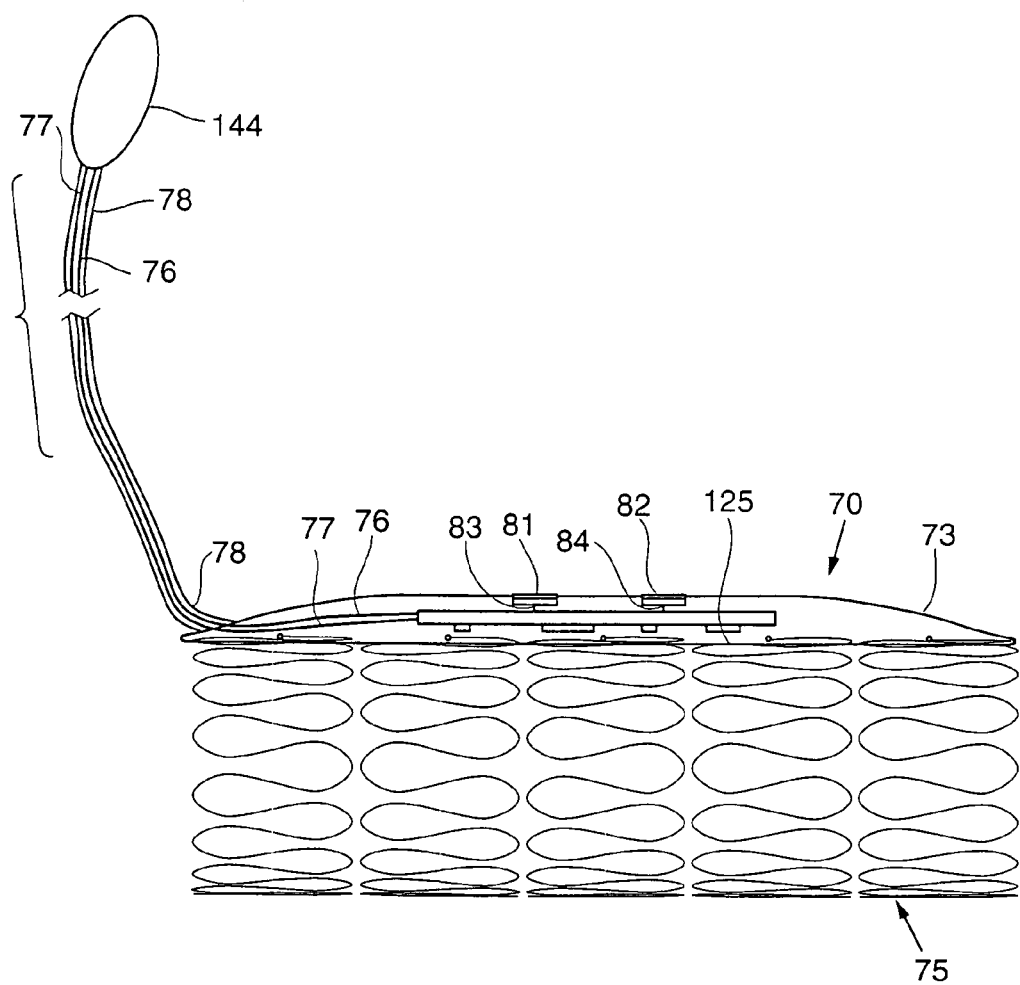
FIG. 2 is an alternative electrode housing for the stimulator of FIG. 1 in which electronics are encased in the electrode housing.

Referring to FIG. 2, an alternative stimulator 70 having an alternative electronics/electrode housing 73 is illustrated. The stimulator 70 comprises a fixation device 75 with a housing 73 for the electrodes 81, 82. The fixation device 75 is similar to fixation device 34 described above with reference to FIGS. 1-1F. The housing 73 in this embodiment also contains the electronics 125. The electrodes 81, 82 are coupled to the electronic circuitry 125 by way of connectors 83, 84. The electronic circuitry 125 is coupled to leads 76, 77 encased in corrosion resistant wire tubing 78 that extends out of the housing 73 and fixation device 75. When the stimulation device 70 is deployed in the duodenum 24, wire tubing 78 similarly extends out of the duodenum 24 in an orad direction, through the pylorus 23 and into the stomach 20 where it is coupled to the battery 144 contained in a battery housing. The fixation device 75 is placed in the duodenum 24 in a manner similar to fixation device 34 described above with reference to FIGS. 1-1F. The battery housing 74 is configured similarly to the electronics housing 50 of FIGS. 1-1F of a corrosion resistant material and rounded configuration, with the battery 144 but without the electronic circuitry 125. The battery 144 is electrically coupled through leads 76, 77 to the electronic circuitry 125 located in the housing 73. The battery housing 74 is removable and replaceable in a manner similar to electronics housing 50 described above with reference to FIGS. 1-1F and the stimulation-programming and protocol may be delivered in a similar manner as well.

Figure 3:
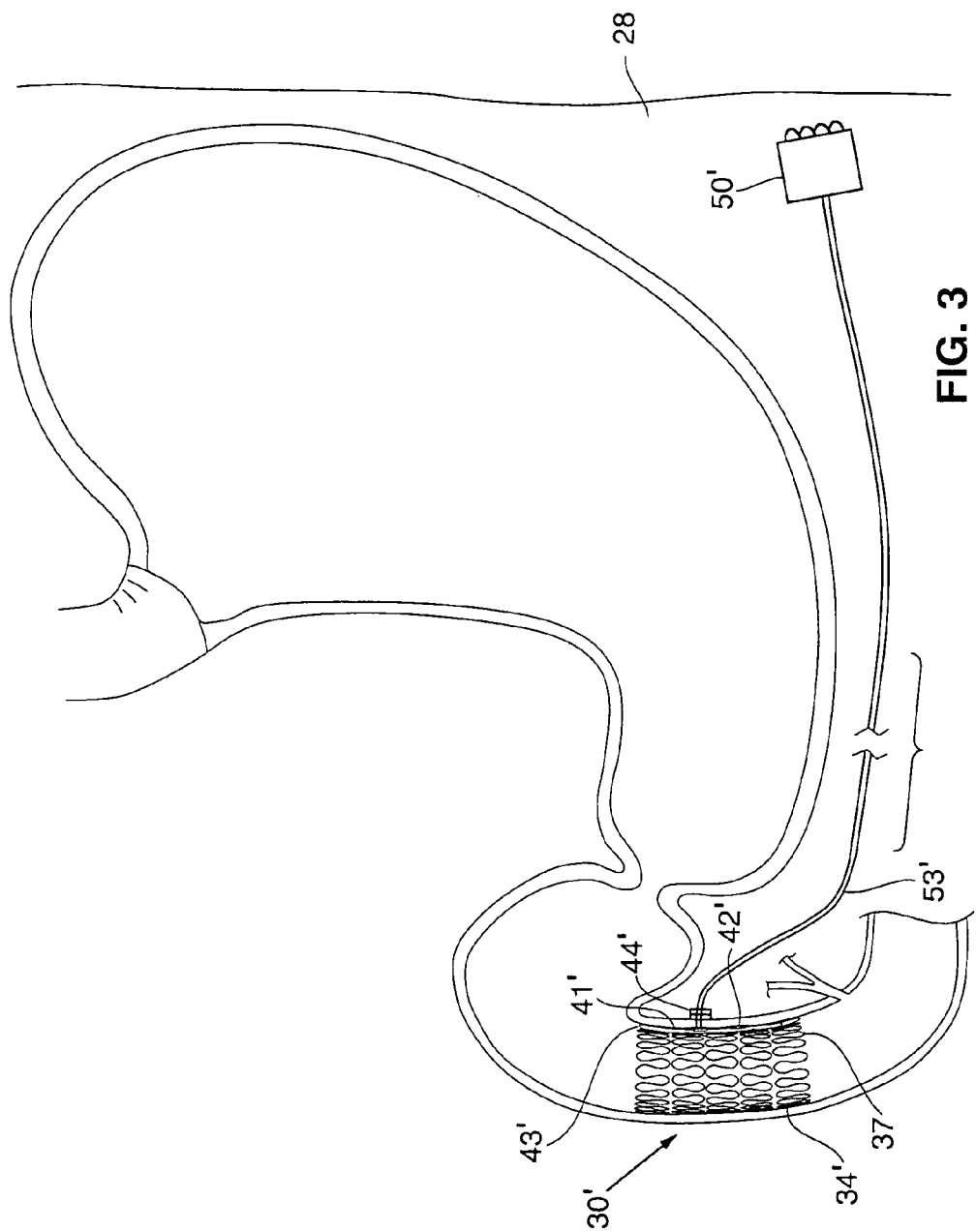
FIG. 3 illustrates another embodiment of an implanted stimulator according to the invention.

Referring to FIG. 3 an alternative stimulator 30' is illustrated comprising a fixation device 34' implanted in a duodenum 24 in a similar manner as fixation device 34 described above with reference to FIGS. 1-1F. In this embodiment however, the wire tubing 53' extends out of the wall 27 of the duodenum 24, into the abdominal cavity 28 where it is coupled to electronics housing 50' containing the electronics unit 125 and battery 144. In implanting the stimulator 30', the fixation device 34' is placed in the duodenum 24 and the electronics housing 50' is implanted subcutaneously within the abdominal cavity 28. The wire tubing 53' coupled to and extending from the electronics housing 50' is then laparoscopically placed through the abdomen and through the wall 27 of the duodenum 24 where it is coupled through connector 44' to the electrodes 41', 42' encased in the electrode housing 43'. The stimulation is provided from the electronic circuitry 125 to the inner wall of the duodenum 24 wall in a manner similar to that described above with reference to FIGS. 1-1F, 5 and 6.

Referring to FIG. 3 an alternative stimulator 30' is illustrated comprising a fixation device 34' implanted in a duodenum 24 in a similar manner as fixation device 34 described above with reference to FIGS. 1-1F. In this embodiment however, the wire tubing 53' extends out of the wall 27 of the duodenum 24, into the abdominal cavity 28 where it is coupled to electronics housing 50' containing the electronics unit 125 and battery 144. In implanting the stimulator 30', the fixation device 34' is placed in the duodenum 24 and the electronics housing 50' is implanted subcutaneously within the abdominal cavity 28. The wire tubing 53' coupled to and extending from the electronics housing 50' is then laparoscopically placed through the abdomen and through the wall 27 of the duodenum 24 where it is coupled through connector 44' to the electrodes 41', 42' similarly encased in the electrode housing 43' as electrodes 41, 42 are encased in housing 43 with reference to FIGS. 1, and 1A-1F. The stimulation is provided from the electronic circuitry 125 to the inner wall of the duodenum 24 wall in a manner similar to that described above with reference to FIGS. 1-1F, 5 and 6.

Figure 4:
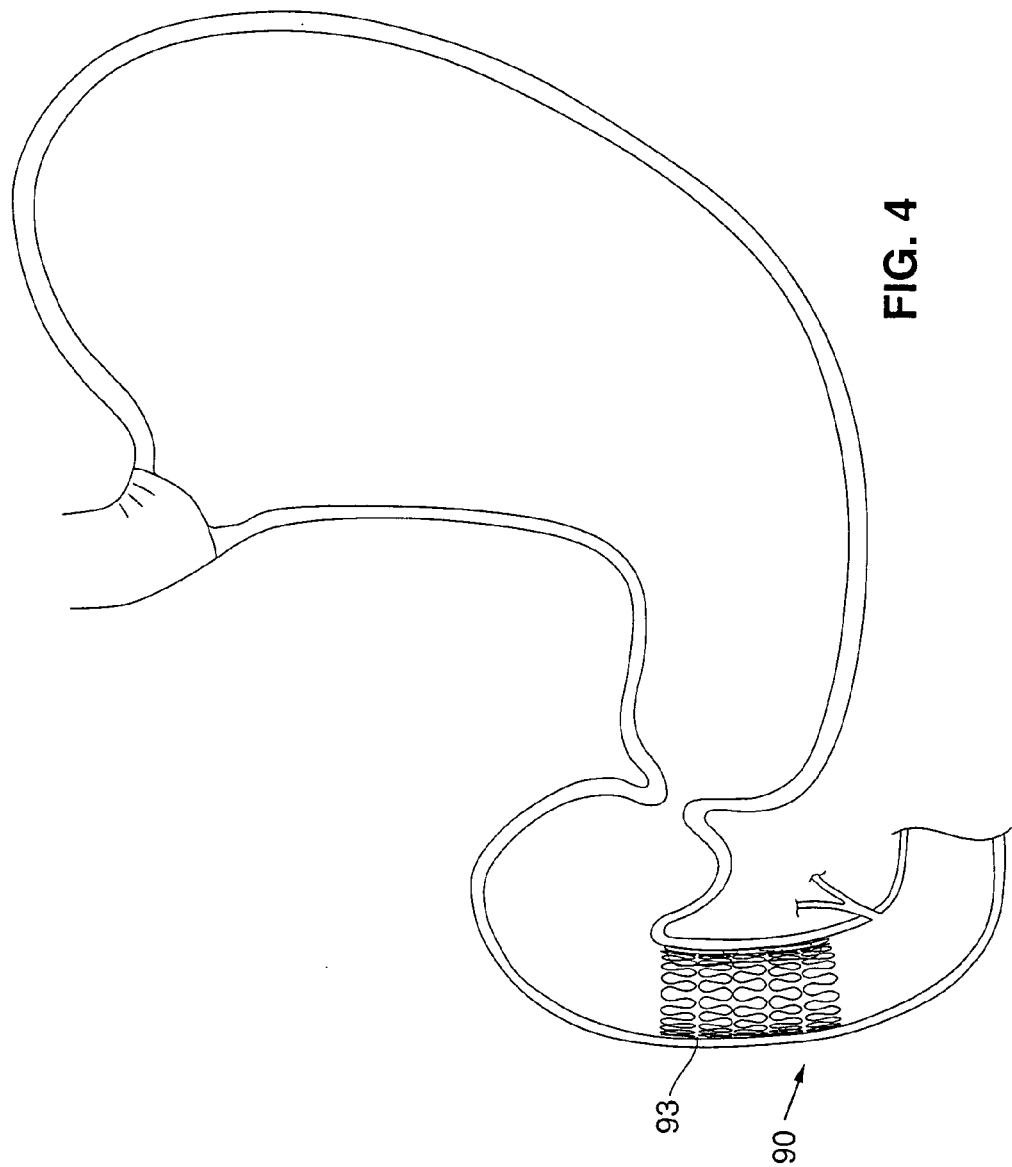
FIG. 4 illustrates another embodiment of an implanted stimulator according to the invention.
Figure 4A:
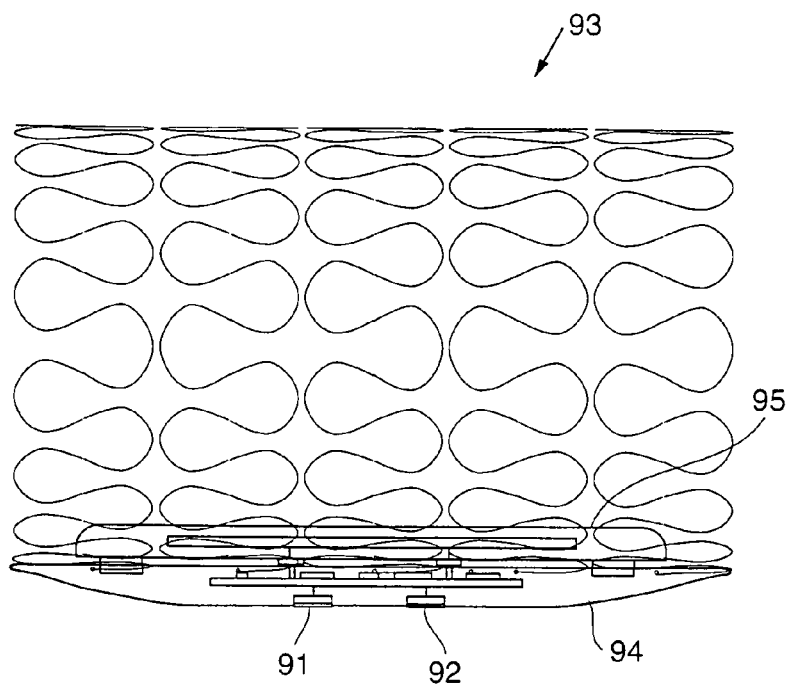
FIG. 4A is a side view of the fixation device of the stimulator of FIG. 4 in an expanded configuration with a removable replaceable battery unit coupled to the electrode housing.
Figure 4B:
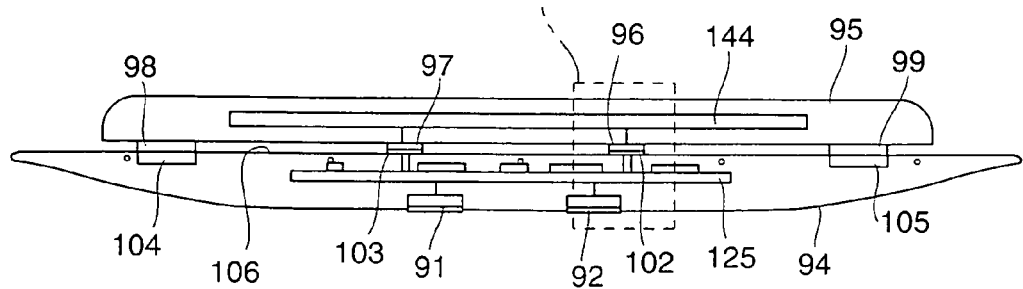
FIG. 4B is a side view of the electrode housing and removable battery unit of the stimulator of FIG. 4A.
Figure 4C:
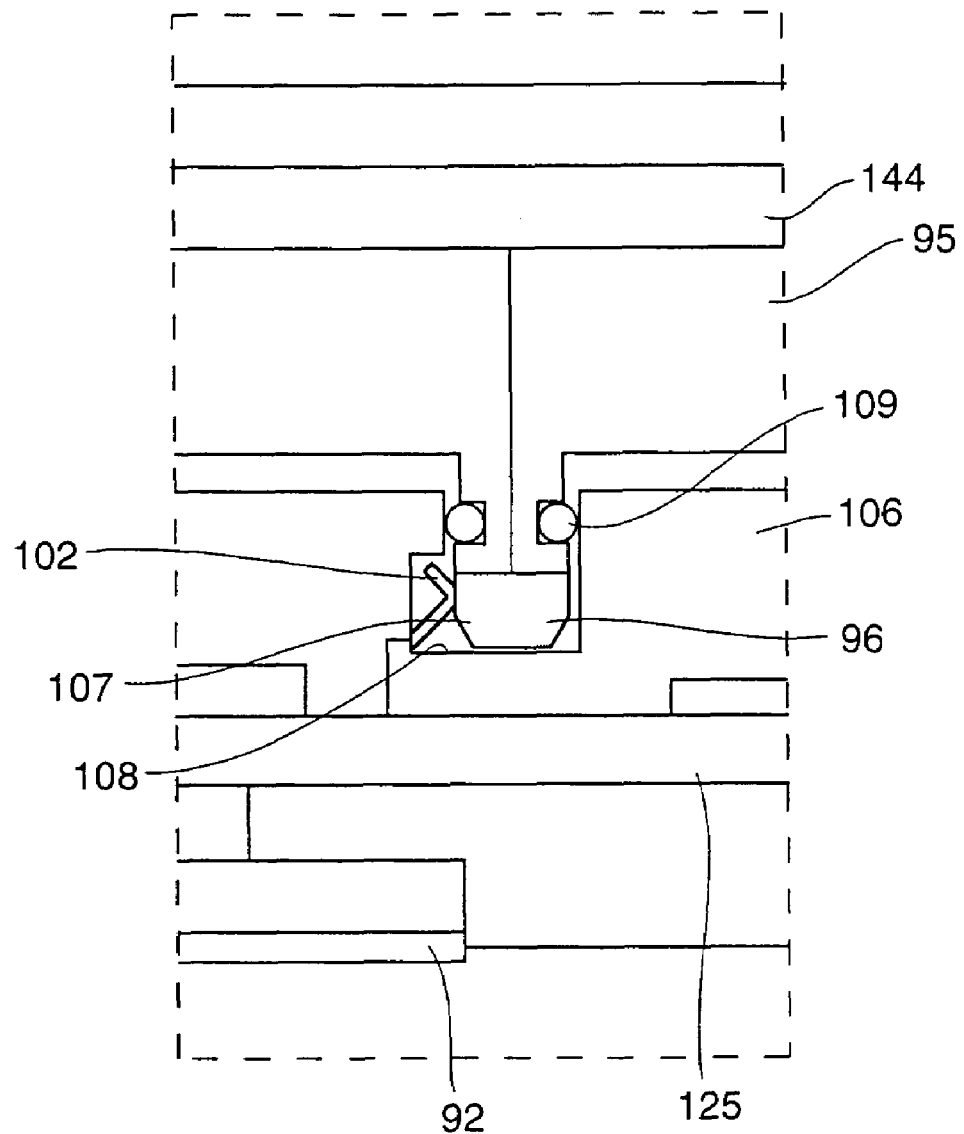
FIG. 4C is an enlarged portion of FIG. 4B as indicated in FIG. 4B.

Referring to FIGS. 4, and 4A-4C, an alternative embodiment of the invention is illustrated. A stimulator 90 comprises a fixation device 93 including an electronics housing 94 with electrodes 91,92 and electronic circuitry 125 coupled to the electrodes 91, 92. The electronic circuitry 125 is powered by battery 144 contained in a removable battery housing 95 that is configured to be removably coupled to the fixation device 93 in electrical communication with the electronics unit 125 contained in the electronics housing 94. In particular, the battery housing 95 includes magnets 98,99 that may be coupled with magnets 104, 105 on the inner wall 106 of the electronics housing 94. Electrical contacts 96,97 on the battery housing 95 align with electrical contacts 102, 103 on the inner wall 106 of the electronics housing 94 when the magnets 98,99 are correspondingly aligned with magnets 104, 105 on the electronics housing 94. When the magnets 98,99 are aligned with magnets 104, 105 and the battery housing is coupled to the electronics housing 94, contacts 96, 97 are correspondingly electrically coupled to contacts 102, 103 so that the battery 144 provides power to the electronic circuitry 125 among other things, to deliver stimulating pulses to the duodenum 24 as described herein with reference to FIGS. 5 and 6. As shown in FIG. 4C, contact 96 comprises a protruding portion 107 that is positioned in recess 108 in inner wall 106 in electronics housing 94. Contact 102 engages protruding member 107 so that electrical contact is made with contact 96. O-ring 109 seals electrical contacts within recess 108.

While the invention has been described with reference to particular embodiments, it will be understood to one skilled in the art that variations and modifications may be made in form and detail without departing from the spirit and scope of the invention.

What is claimed is:

1. A method for treating obesity comprising the steps of:
   implanting a stimulator in a duodenum of a patient in a manner that allows passage of material through the duodenum;
   providing electrical stimulation to the duodenum of the patient, for a predetermined period of time after ingestion of a meal, to control contraction of a pylorus of the patient and thereby treat obesity.

2. The method of claim 1 further comprising the steps of sensing ingestion of food into the stomach prior to providing stimulation.

3. A method for treating obesity comprising:
   providing a stimulator comprising:
      a fixation device including a radially expandable member and an outer portion;
      at least one electrode coupled to the outer portion of the fixation device; and
      electronic circuitry coupled to the at least one electrode and configured to deliver electrical stimulation through the at least one electrode;
   implanting the stimulator in a duodenum of a patient in a manner that allows passage of material through the duodenum by;
      positioning the fixation device in the duodenum of a patient so that the at least one stimulating electrode is in electrical contact with the wall of the duodenum; and fixing the fixation device with the radially expandable member within a portion of a gastrointestinal tract so that the electrode is in electrical contact with the gastrointestinal tract; and providing electrical stimulation to the duodenum of a patient to control the contraction of the pylorus and thereby treat obesity, wherein providing electrical stimulation comprises providing stimulation pulses from the electronic circuitry to the duodenum through the at least one electrode and thereby affecting the contraction of the pylorus.

4. The method of claim 1 wherein the step of stimulating the duodenum comprises stimulating the duodenum to cause gastric retention of food.

5. A device for treating obesity comprising:
 a stimulator comprising:
  a fixation device;
  at least one electrode coupled to the fixation device; and
  a sensor configured to sense ingestion of food by a patient;
  electronic circuitry coupled to the at least one electrode and the sensor and configured to deliver electrical stimulation through the at least one electrode, the electronic circuitry comprising a responsive element configured to provide stimulation to a duodenum after sensing ingestion of food by the patient;
 the fixation device configured to fix the stimulator in the duodenum of a patient so that the at least one stimulating electrode is in electrical contact with the wall of the duodenum while permitting movement of material through the duodenum.

6. The device of claim 5 wherein the responsive element is configured to provide stimulation for a predetermined amount of time.

* * * * *